US012779111B2

(12) United States Patent
Yang

(10) Patent No.: US 12,779,111 B2
(45) Date of Patent: Nov. 3, 2026

(54) SKIN PATCH DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 545 days.

(21) Appl. No.: 18/268,247

(22) PCT Filed: Jul. 2, 2021

(86) PCT No.: PCT/CN2021/104147
§ 371 (c)(1),
(2) Date: Jun. 19, 2023

(87) PCT Pub. No.: WO2022/147985
PCT Pub. Date: Jul. 14, 2022

(65) Prior Publication Data

US 2024/0050649 A1 Feb. 15, 2024

(30) Foreign Application Priority Data

Jan. 5, 2021 (CN) ........................ 202110008701.X
Jan. 5, 2021 (WO) ................ PCT/CN2021/070207

(51) Int. Cl.
*A61M 5/142* (2006.01)
*A61M 5/145* (2006.01)
(Continued)

(52) U.S. Cl.
CPC .... *A61M 5/14248* (2013.01); *A61M 5/14236* (2013.01); *A61M 5/1452* (2013.01);
(Continued)

(58) Field of Classification Search
CPC .......... A61M 5/14248; A61M 5/14236; A61M 5/1452; A61M 5/1454; A61M 5/1456;
(Continued)

(56) References Cited

U.S. PATENT DOCUMENTS 6,589,229 B1 7/2003 Connelly et al.
10,279,106 B1 5/2019 Cook et al.
(Continued)

FOREIGN PATENT DOCUMENTS

CN 101522235 9/2009
CN 204910157 12/2015
CN 110545862 12/2019

OTHER PUBLICATIONS

"International Search Report (Form PCT/ISA/210) of PCT/CN2021/104147", mailed on Sep. 28, 2021, pp. 1-3.

*Primary Examiner* — James D Ponton
(74) *Attorney, Agent, or Firm* — JCIP GLOBAL INC.

(57) ABSTRACT

A skin patch drug infusion device, includes a control mechanism module provided with multiple first engaging portions and a first electrical connection exposed on the surface of the control mechanism module; and an infusion mechanism module including a case, with a second electrical connection exposed on the surface of the case and second engaging portions that engaged with the first engaging portions; and an alarm, non-closed arranged in the control mechanism module. When the control mechanism module and the infusion mechanism module are assembled with each other, the first engaging portions and the second engaging portions are engaged, the first electrical connection and the corresponding second electrical connection are electrically connected to each other, thereby the control mechanism module and the infusion mechanism module are electrically connected to each other.

15 Claims, 4 Drawing Sheets

(51) Int. Cl.
*A61M 5/168* (2006.01)
*A61M 5/172* (2006.01)
*A61M 99/00* (2012.01)

(52) U.S. Cl.
CPC ........ *A61M 5/1454* (2013.01); *A61M 5/1456* (2013.01); *A61M 5/16831* (2013.01); *A61M 5/172* (2013.01); *A61M 5/1723* (2013.01); *A61M 99/00* (2022.08); *A61M 2005/14208* (2013.01); *A61M 2005/14252* (2013.01); *A61M 2005/14268* (2013.01); *A61M 2005/14506* (2013.01); *A61M 2202/0007* (2013.01); *A61M 2202/04* (2013.01); *A61M 2205/02* (2013.01); *A61M 2205/0216* (2013.01); *A61M 2205/0233* (2013.01); *A61M 2205/0238* (2013.01); *A61M 2205/123* (2013.01); *A61M 2205/18* (2013.01); *A61M 2205/33* (2013.01); *A61M 2205/8206* (2013.01); *A61M 2205/8212* (2013.01); *A61M 2209/088* (2013.01); *A61M 2210/04* (2013.01); *A61M 2230/201* (2013.01)

(58) Field of Classification Search
CPC .............. A61M 5/16831; A61M 5/172; A61M 5/1723; A61M 99/00; A61M 2005/14208; A61M 2005/14252; A61M 2005/14268; A61M 2005/14506; A61M 2202/0007; A61M 2202/04; A61M 2205/02; A61M 2205/0216; A61M 2205/0233; A61M 2205/0238; A61M 2205/123; A61M 2205/18; A61M 2205/33; A61M 2205/8206; A61M 2205/8212; A61M 2209/088; A61M 2210/04; A61M 2230/201; A61M 5/1413; A61M 2205/106; A61M 2205/505; A61M 2205/586; A61M 2230/63; A61B 2560/0456; A61B 2562/225; A61B 5/14503; A61B 5/14532; A61B 5/4839; A61B 5/6833
See application file for complete search history.

(56) References Cited

U.S. PATENT DOCUMENTS

2002/0169439 A1* 11/2002 Flaherty .................... A61P 9/10
604/891.1
2011/0319729 A1* 12/2011 Donnay ............. A61B 5/14546
600/309
2014/0296787 A1* 10/2014 Agard ................... A61M 5/172
604/152
2017/0332980 A1* 11/2017 Fifield .................. A61B 5/7282

* cited by examiner

SKIN PATCH DRUG INFUSION DEVICE

CROSS-REFERENCE TO RELATED APPLICATION

This application is a 371 of international application of PCT application serial no. PCT/CN2021/104147, filed on Jul. 2, 2021, which claims the priority benefit of PCT application no. PCT/CN2021/070207, filed on Jan. 5, 2021 and the priority benefit of China application no. 202110008701.X, filed on Jan. 5, 2021. The entirety of each of the above mentioned patent applications is hereby incorporated by reference herein and made a part of this specification.

TECHNICAL FIELD

The present invention mainly relates to the field of medical instruments, in particular to a skin patch drug infusion device.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose.

However, at present the alarm is entirely enclosed in the control mechanism module of the infusion device, such as, a louder sound signal, need to emitted from the alarm to raise the user's attention, which increases the energy consumption of the alarm.

Therefore, in the prior art, there is an urgent need for a drug infusion device with low energy consumption.

BRIEF SUMMARY OF THE INVENTION

The invention discloses a skin patch drug infusion device. The alarm is non-closed arranged in the control mechanism module, reducing the energy consumption of the alarm, optimizing the power consumption configuration of the infusion device and saving production costs.

The invention discloses a skin patch drug infusion device, which comprises: a control mechanism module provided with multiple first engaging portions and a first electrical connection exposed on the surface of the control mechanism module; and an infusion mechanism module including a case, with a second electrical connection exposed on the surface of the case and second engaging portions that engaged with the first engaging portions, when the control mechanism module and the infusion mechanism module are assembled with each other, the first engaging portions and the second engaging portions are engaged, the first electrical connection and the corresponding second electrical connection electrically connected to each other, thereby electrically connecting the control mechanism module and the infusion mechanism module; and an alarm, non-closed arranged in the control mechanism module.

According to one aspect of the present invention, the alarm is one or a combination of lighting alarm, audio alarm and vibration alarm, or an alarm with multiple alarm signals of light, sound, or vibration.

According to one aspect of the present invention, the alarm is a buzzer.

According to one aspect of the present invention, at least a non-closed area is provided in the housing of the control mechanism module.

According to one aspect of the present invention, the non-closed area is a sound-permeable outlet.

According to one aspect of the present invention, the control mechanism module includes an upper housing and a lower housing, the sound-permeable outlet is arranged on the lower housing.

According to one aspect of the present invention, a waterproof sound-permeable membrane is disposed between the sound-permeable outlet and the buzzer.

According to one aspect of the present invention, the first engaging portions and the second engaging portions include one or more of hooks, blocks, holes, or slots that engaged with each other.

According to one aspect of the present invention, the first engaging portions and the second engaging portions are multiple first electrical contacts and multiple second electrical contacts.

According to one aspect of the present invention, one of the first electrical contacts or the second electrical contacts is a rigid metal pin or an elastic conductive member.

According to one aspect of the present invention, the type of the elastic conductive member includes conductive spring, conductive leaf spring, conductive rubber, or conductive silica gel.

According to one aspect of the present invention, one of the first electrical contacts is a rigid metal pin while one of the second electrical contacts is a conductive spring, a groove, within which a sealing element is provided, is disposed around the area where multiple second electrical contacts are disposed.

According to one aspect of the present invention, a plurality of connection ends is provided in the infusion mechanism module, and a plurality of compressed conductive springs are respectively electrically connected to the corresponding connection ends.

According to one aspect of the present invention, a flexible circuit board on which the connection ends are disposed is further provided in the infusion mechanism module.

According to one aspect of the present invention, the case includes upper case and lower case.

According to one aspect of the present invention, the lower case further includes an outward extending portion, and a block is provided on the outside of the outward extending portion.

According to one aspect of the present invention, a pressing portion is provided on the outside end of the outward extending portion.

Compared with the prior art, the technical solution of the present invention has the following advantages:

In the skin patch drug infusion device disclosed by the present invention, the alarm is non-closed arranged in the control mechanism module, reducing the energy consumption of the alarm, optimizing the power consumption configuration of the infusion device and saving production costs.

Furthermore, a waterproof sound-permeable membrane is disposed between the sound-permeable outlet and the buzzer, which has high level waterproof and dustproof capacity, the protect grade can reach to IP68.

Furthermore, a control mechanism module provided with multiple first engaging portions and first electrical contacts exposed on the surface of the control mechanism module; the infusion mechanism module is provided with a plurality of second electrical contacts exposed on the surface of the case. The contact area of the electrical contact is small, which facilitates the mechanism module design and helps reducing the volume of the control mechanism module. Secondly, when the first engaging portions and the second engaging portions are engaged, the first electrical contact and the corresponding second electrical contact press against each other, thereby electrically connecting the control mechanism module and the infusion mechanism module. The control mechanism module and the infusion mechanism module are electrically connected to each other through the two kinds of electrical contacts pressing against each other, which facilitates the optimization of the circuit design and helps improving the reliability of the electrical connection.

Furthermore, the type of the elastic conductive member includes conductive spring, conductive leaf spring, conductive rubber, or conductive silica gel. An elastic conductive member, compared with a fixed contact, can further increase the reliability of the electrical connection.

Furthermore, a flexible circuit board on which the connection ends are disposed is further provided in the infusion mechanism module. The shape of the flexible circuit board can be flexibly designed according to the internal mechanism module features in the infusion mechanism module, which helps optimizing the internal design of the infusion mechanism module.

Furthermore, the lower case further includes an outward extending portion, and a block is provided on the outside of the outward extending portion. The block can prevent the control mechanism module from detaching from the infusion mechanism module.

DETAILED DESCRIPTION

Figure 1A:
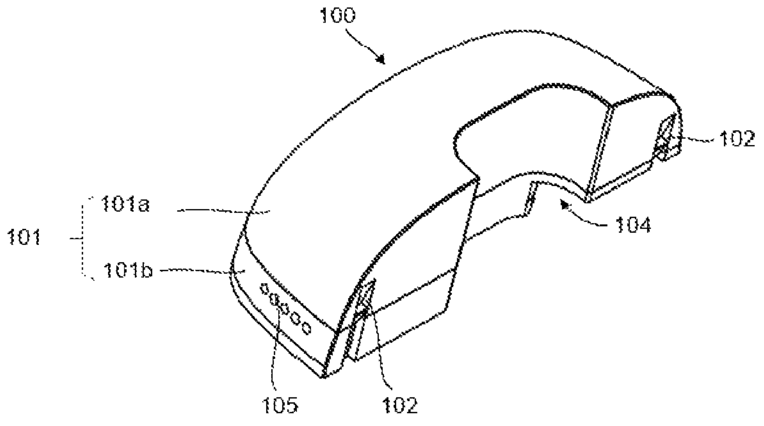
FIG. 1*a* is a schematic view of the control mechanism module from the front side according to an embodiment of the present invention.

As mentioned above, in the prior art, the alarm is entirely enclosed in the control mechanism module of the infusion device, such as, a louder sound signal, need to emitted from the alarm to raise the user's attention, the energy consumption of the fusion device is relatively large.

In order to solve this problem, the present invention provides a drug infusion device. The alarm is non-closed arranged in the control mechanism module, reducing the energy consumption of the alarm, optimizing the power consumption configuration of the infusion device and saving production costs.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the FIGURES are not necessarily drawn in the actual scale relationship, for example, the thickness, width, length or distance of certain units may be exaggerated relative to other mechanism modules.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following FIGURES. Therefore, once an item is defined or illustrated in a drawing, it will not be discussed further in following description of the drawings.

Figure 1B:
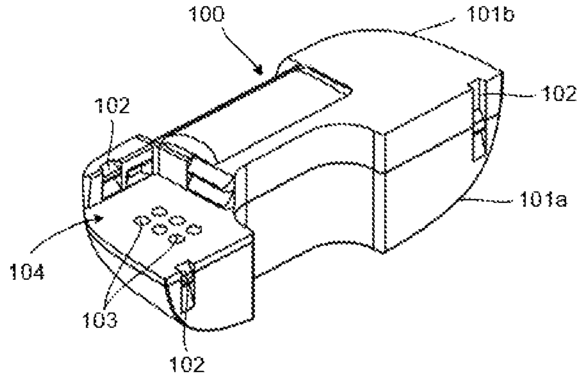
FIG. 1*b* is a schematic view of the control mechanism module from the bottom side according to an embodiment of the present invention.
Figure 1C:
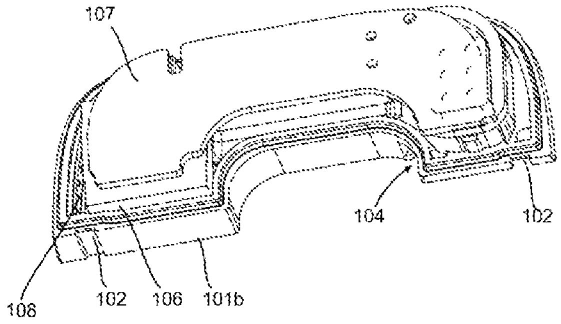
FIG. 1*c* is schematic view of the control mechanism module without upper housing from the front side according to an embodiment of the present invention.

FIG. 1*a* is a schematic view of the control mechanism module from the front side according to an embodiment of the present invention; FIG. 1*b* is a schematic view of the control mechanism module from the bottom side according to an embodiment of the present invention; FIG. 1*c* is schematic view of the control mechanism module without upper housing 101*a* from the front side according to an embodiment of the present invention.

The skin patch drug infusion device of the embodiment of the present invention includes two main parts: a control mechanism module 100 and an infusion mechanism module 110, which will be described separately in detail below. And in another embodiment of the present invention, the skin patch drug infusion device can be provided with more than two parts, which is not specifically limited herein.

Figure 2A:
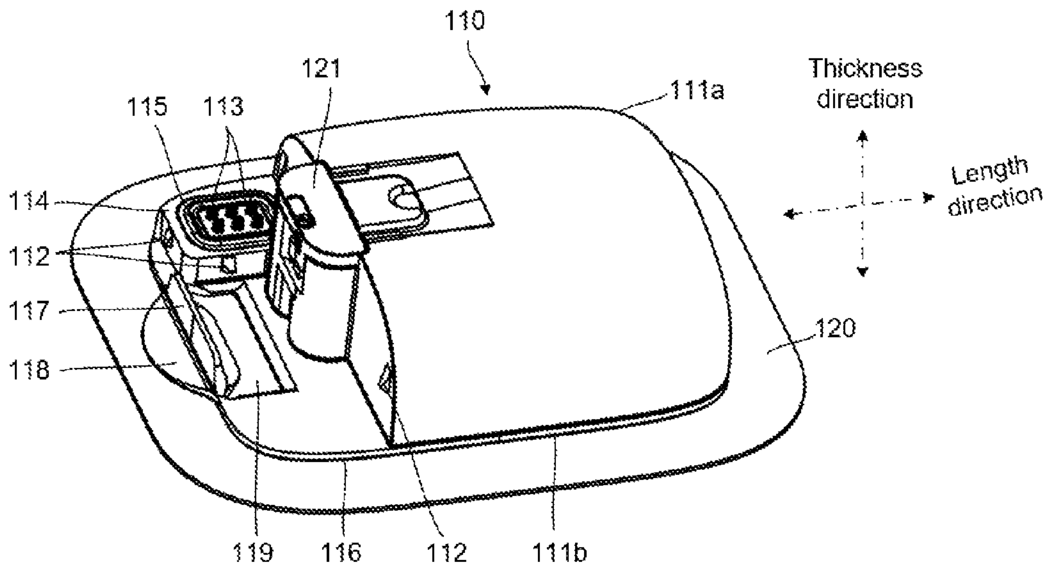
FIG. 2*a* is a schematic view of the infusion mechanism module according to an embodiment of the present invention.
Figure 2B:
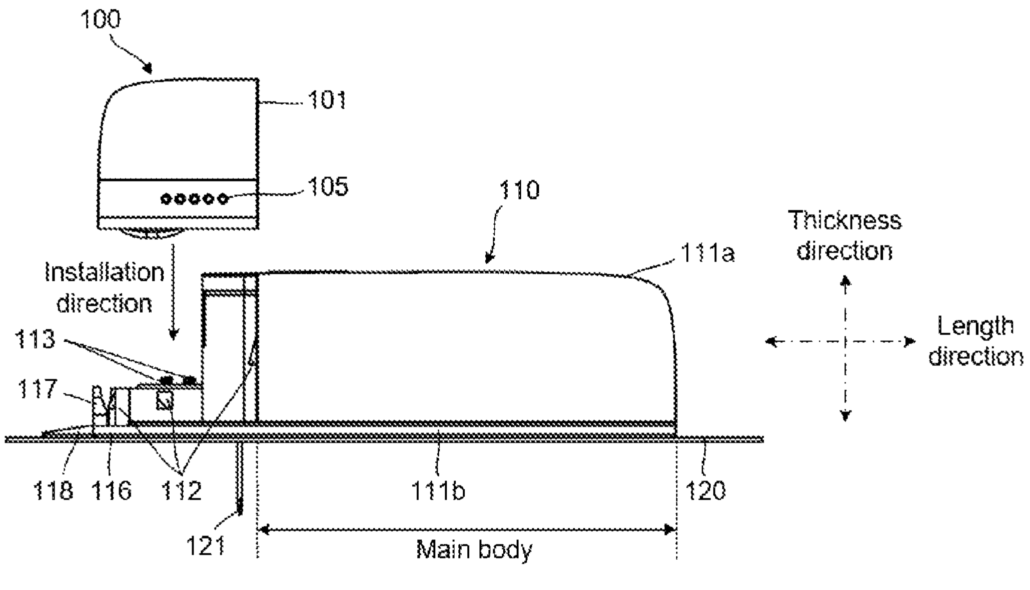
FIG. 2*b* is a side view of the assembly of the control mechanism module and the infusion mechanism module according to an embodiment of the present invention.
Figure 3A:
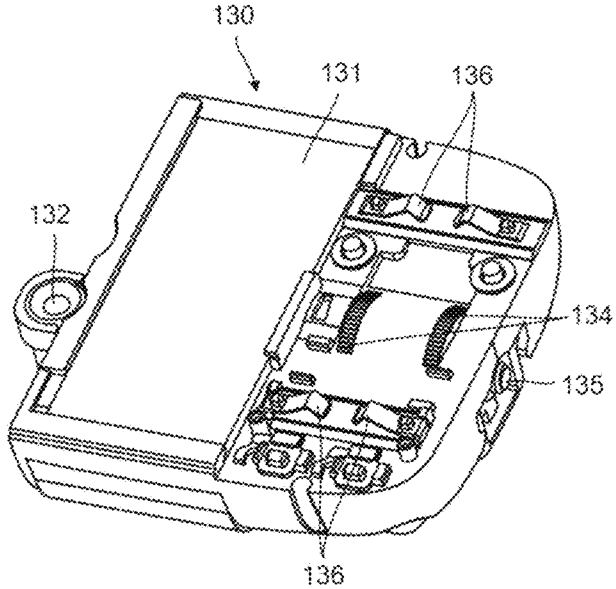
FIG. 3*a* and FIG. 3*b* are respectively schematic views of the internal mechanism module of the infusion mechanism module according to an embodiment of the present invention.
Figure 3B:
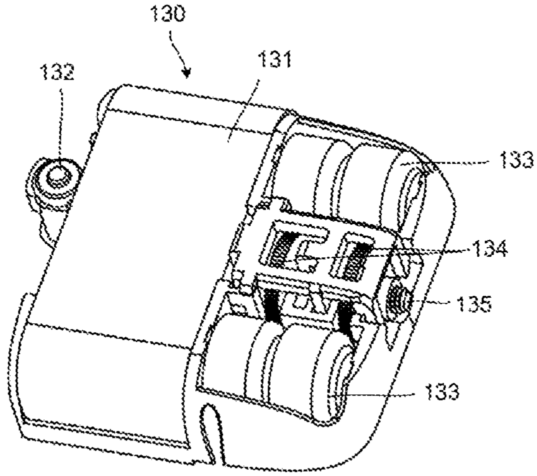

The skin patch drug infusion device refers to a tubing-free infusion device that is entirely pasted on the user's skin surface by the one piece of medical tape 120 (as shown in FIG. 2*a* and FIG. 2*b*). And the infusion device is provided with an infusion needle unit 121 (as shown in FIG. 2*a* and FIG. 2*b*), integrated on the infusion device, instead of a long tube, therefore, drug can be directly infused from the drug reservoir 131 (as shown in FIG. 3*a* and FIG. 3*b*) to the subcutaneous tissue through the infusion needle unit 121.

The skin patch drug infusion device of the embodiment of the present invention includes a control mechanism module 100 which receives signals or information from a remote device or a body fluid parameter detection device (such as CGM), and controls the infusion device to infuse drug(s) accordingly.

Inside the housing 101 of the control mechanism module 100 are disposed program modules, circuit board(s) 107 and related electronic units for receiving signals or issuing control instructions, as well as other mechanical units or structures necessary for realizing the infusion function, which is not limited herein. The housing 101 includes an upper housing 101*a* and a lower housing 101*b*. In another embodiment of the present invention, a power supply 133 can be also provided in the control mechanism module. Preferably, in the embodiment of the present invention, the power supply 133 is provided in the infusion mechanism module 110, which will be described below.

The control mechanism module 100 further includes a first electrical connection 103 exposed on the surface of it. The first electrical connection 103 is used as circuit connection terminal for electrically connecting the internal circuits provided in the control mechanism module 100 and the infusion mechanism module 110, respectively. The embodiment of the present invention does not specifically limit the positions of first electrical connection 103.

Preferably, in the embodiment of the present invention, the first electrical connection 103 is multiple first electrical contacts 103. Compared with the plug connector used as connection terminal in the prior arts, the contact area of the electrical contact is much smaller, which provides more flexibility to the mechanism module design, and can effectively reduce the volume of the control mechanism module. At the same time, these smaller electrical contacts can be directly electrically connected to the internal circuit or electrical components, or can be directly soldered on the circuit board, which helps to optimize the design of the internal circuit and effectively reduce the complexity of the circuit, thereby, saving costs and reducing the volume of the infusion device. Furthermore, the electrical contacts are exposed on the surface of the control mechanism module 100 to facilitate electrical connection with connection ends on other mechanism modules.

The type of the first electrical contact 103 includes rigid metal pins or elastic conductive members. Preferably, in the embodiment of the present invention, the first electrical contact 103 is a rigid metal pin. One end of the first electrical contact 103 is electrically connected to the connection end provided inside the control mechanism module 100 while the other end is exposed on the surface of the lower housing 101*b*. And the rest part of the first electrical contact 103 is tightly embedded in the housing 101, thus keeping the inside of the control mechanism module 100 isolated from the outside.

Here, the type of the elastic conductive member includes conductive spring, conductive silica gel, conductive rubber, or conductive leaf spring. Obviously, one end of the elastic conductive member is used to electrically connect with the internal connection end in the control mechanism module 100 while the other end is used to electrically connect with other connection ends. As in an embodiment of the present invention, the first electrical contact 103 is a conductive spring. When the electrical contacts are in contact with each other, the elasticity of the conductive spring can enhance the reliability of the electrical connection. Similar to the rigid metal pin, one end of the conductive spring is exposed on the surface of the lower housing 101*b*, while the rest part of the conductive spring is tightly embedded in the housing 101 and electrically connected with internal circuits or electrical components. Obviously, the connection end disposed inside the control mechanism module 100 can be a conductive lead, a specific part of a circuit, or an electrical element.

It should be noted that the "tightly embedded" in the embodiment of the present invention means that there is no gap between the electrical contact and the housing 101, keeping the control mechanism module 100 tightly sealed. The following "tightly embedded" has the same meaning as here.

In another embodiment of the present invention, the first electrical contact 103 is a conductive spring, but it is not tightly embedded in the housing 101. Instead, a sealing element is provided in a groove, both of which are disposed around the area where the first electrical contacts 103 are located, thus, sealing the electrical contact area and the control mechanism module 100.

In the embodiment of the present invention, the control mechanism module 100 is further provided with first engaging portions 102 which is used to fasten with the second engaging portion 112 disposed on the infusion mechanism module 110 to assemble the control mechanism module 100 and the infusion mechanism module 110, thereby enabling the electrical connection between the first electrical contacts 103 and the second electrical contacts 113 (as shown in FIG. 2*a* and FIG. 2*b*), which will be described in detail below.

The first engaging portion 102 and the second engaging portion 112 include one or more of hooks, blocks, holes, and slots that can be engaged with each other. The positions of the hooks, blocks, holes, and slots can be flexibly adjusted according to the shape and mechanism module features of the control mechanism module 100 and the infusion mechanism module 110, such as disposed in the interior or on the surface of the corresponding mechanism module, which is not specifically limited herein.

In the embodiment of the present invention, the control mechanism module 100 is further provided with a concave 104 that fits the convex portion 114 disposed at the bottom of the case of the infusion mechanism module 110, which will be described in detail below. Preferably, the first electrical contacts 103 are provided in the concave 104, as shown in FIG. 1*b*.

In the embodiment of the present invention, an alarm is non-closed provided in the control mechanism module 100, at least a non-closed area is also provided on the housing 101 of the control mechanism module 100. When the infusion process starts or ends, the infusion device malfunctions, the drug is exhausted, the control mechanism module 100 issues an error command or receives an error message, etc., the alarm is used to issue alarm signals, such as light, sound or vibration, notifying the user to adjust or replace the device in time. The alarm can be one or more of lighting lights, audio alarms, and vibration alarms, which is not specific limited here.

In the embodiment of the present invention, the non-closed area provided on the housing 101 of the control structure 100 is one or more openings, which can be a circle, a square, a triangle, a polygon, an irregular shape or any arbitrary shape, and arranged in a single row, multiple rows or any other random arrangement. The location of the non-enclosed area on the housing 101 of the control mechanism module 100 is not limited. Specifically, it may only be provided on the upper housing 101*a* or the lower housing 101*b*, or provided on the upper housing 101*a* and the lower housing 101*b* at the same time. The location of the non-closed area on the upper housing 101*a* or the lower housing 101*b* is also not limited. Specifically, it can be provided on the top, front, left or right side of the upper housing 101*a* or the lower housing 101*b*. It can also be provided on only one side, or provided on multiple sides at the same time. The number, shape, and arrangement of the non-closed area on each side are not limited, it can be the same or different. That is, the location, shape, size, number, and arrangement of the non-closed area are not limited here, as long as the alarm signal can be sent out from it. Preferably, in the embodiment of the present invention, the non-enclosed area is an opening provided along the edge of the alarm, that is, the location of the non-enclosed area is adapted to the position of the alarm, which makes it easier for the alarm signal to be sent out and raise the user's attention, reducing the energy consumption of the alarm, optimizing the power consumption configuration of the infusion device and saving production costs.

As the alarm is non-closed provided in the control mechanism module 100, compared with the traditional technical solution in which the alarm is entirely enclosed in the control mechanism module 100, when the alarm is a audio alarm, a less loud sound signal emitted from the alarm would be enough to raise the user's attention, which reduces the energy consumption of the audio alarm; When the alarm is a lighting alarm, it will be easier for the light to emit from the non-enclosed area and to raise the attention of the user, which reduces the energy consumption of the alarm. Especially, when the housing 101 of the control mechanism module 100 only can be made of a material with poor light transmission, more energy consumption of the alarm can be reduced as the light will be much easier to emit from the non-enclosed area. When the alarm is a vibration alarm, the weight of the infusion device is reduced due to the existence of the non-enclosed area, and the alarm requires only a small amount of power consumption to generate vibration and be noticed by the user. Based on the above mentioned reasons, when the alarm is a combination of audio alarm, lighting alarm, and vibration alarm, or an alarm that has multiple alarm signals such as lighting, sound, or vibration, as the alarm is non-closed provided in the control mechanism module 100, it will be easier for the alarm signals to emit from the non-enclosed area and to raise the attention of the user, reducing the energy consumption of the alarm, optimizing the power consumption configuration of the infusion device and saving production costs.

Specifically, in the embodiment of the present invention, the alarm is an audio alarm. Preferably, in the embodiment of the present invention, the audio alarm is a buzzer 106, amounted on the circuit board 107 of the control mechanism module 100. When the infusion process starts or ends, the infusion device malfunctions, the drug is exhausted, the control mechanism module 100 issues an error command or receives an error message, etc., the buzzer 106 is used to issue alarm signals, such as sound or vibration, notifying the user to adjust or replace the device in time. More specifically, in the embodiment of the present invention, the buzzer 106 is a piezoelectric buzzer.

Preferably, in the embodiment of the present invention, the non-closed area provided on the lower housing 101*b* of the control mechanism module 100 is a sound-permeable outlet 105 to allow the sound alarm signal from the buzzer 106 to be sent out. As mentioned above, the shape, size, number, arrangement on the housing 101 of the control mechanism module 100 of the sound-permeable outlet 105 are not limited, and will not be described here, as long as the sound alarm signal can be emitted. Preferably, in the embodiment of the present invention, the sound-permeable outlet 105 are a row of dense but separated small holes arranged on the side surface of the lower housing 101*b*. The diameter of the small holes is very small, smaller than the diameter of general water drops, which can prevent water drops from entering the control structure 101. The position of the sound-permeable outlet 105 is adapted to the position of the buzzer 106, and the overall length span is slightly larger than the edge length of the buzzer 106, so that the sound alarm signal of the buzzer 106 can be emitted more easily, reducing the energy consumption of the alarm, optimizing the power consumption configuration of the infusion device and saving production costs.

In order to achieve a good sealing effect and ensure the normal operation of the buzzer, a waterproof sound-permeable membrane 108 is disposed between the sound-permeable outlet 105 and the buzzer 106. Therefore, the waterproof sound-permeable membrane 108 needs to have a certain porosity to ensure the sound transmission but prevent water molecules penetration. Preferably, in the embodiment of the present invention, the waterproof sound-permeable membrane 108 is composed of a lot of small holes with a diameter of 0.1-1 microns, and the waterproof and dustproof grade can reach to IP68.

Compared with the traditional technical solution in which the buzzer is entirely enclosed in the control mechanism module 100, because of the sound-permeable outlet 105 and the waterproof sound-permeable membrane 108, a less loud sound signal emitted from the buzzer would be enough to raise the user's attention, which reduces the energy consumption of the buzzer, thereby optimizing the power consumption configuration of the infusion device and saving production costs.

Figure 2C:
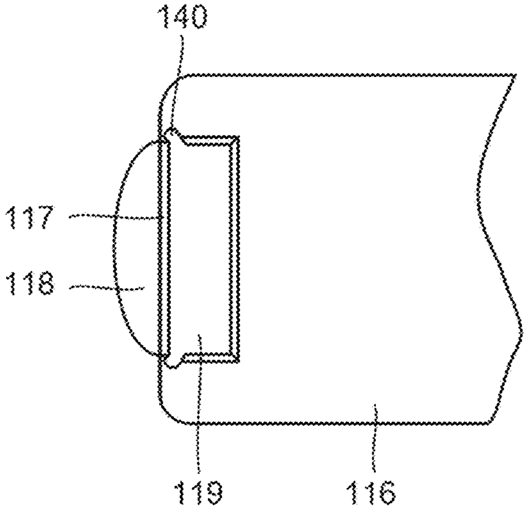
FIG. 2*c* is a schematic top view of the lower case of the infusion mechanism module according to an embodiment of the present invention.
Figure 2D:
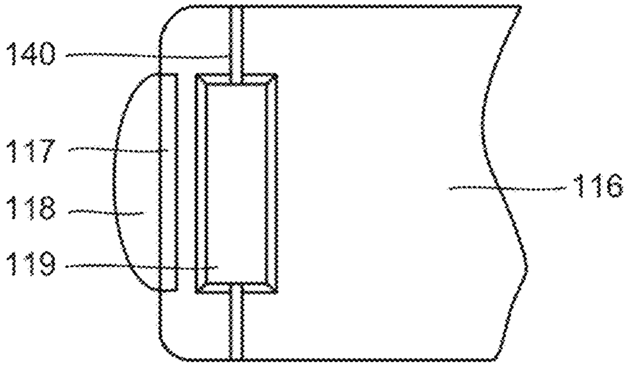
FIG. 2*d* is a schematic top view of the lower case of the infusion mechanism module according to another embodiment of the present invention.

FIG. 2*a* is a schematic view of the infusion mechanism module 110 according to the embodiment of the present invention. FIG. 2*b* is a side view of the assembly of the control mechanism module 100 and the infusion mechanism module 110 according to the embodiment of the present invention. FIG. 2*c* is a schematic top view of the lower case of the infusion mechanism module according to an embodiment of the present invention. FIG. 2*d* is a schematic top view of the lower case of the infusion mechanism module according to another embodiment of the present invention.

The skin patch drug infusion device further includes an infusion mechanism module 110 with a case. A mechanical unit, an electric control unit, and other auxiliary units for completing drug infusion process are provided inside the case, which will be described in detail below. The case of the infusion mechanism module 110 may include multiple parts. As in the embodiment of the present invention, the case of the infusion device includes an upper case 111*a* and a lower case 111*b*.

As mentioned above, in the embodiment of the present invention, the infusion mechanism module 110 is provided with the second engaging portions 112 which is used to engaged and fasten with the corresponding first engaging portions 102. Therefore, the positions where the first engaging portion 102 and the second engaging portion 112 are provided correspond to each other.

In the embodiment of the present invention, the infusion mechanism module 110 is provided with a second electrical connection 113, the second electrical connection 113 is electrically connected to the first second electrical connection 103, thereby electrically connecting the control mechanism module 100 and the infusion mechanism module 100. Preferably, the second electrical connection 113 is multiple second electrical contacts 113. The technical advantages of the electrical contacts are applicable to both the first electrical contacts 103 on the control mechanism module 100 and the second electrical contacts 113 on the infusion mechanism module 110, which will not be described respectively in detail here. The second electrical contacts 113 are used to press against the corresponding first electrical contacts 103 to create electrical connection between the control mechanism module 100 and the infusion mechanism module 110. The mutual pressing between these two corresponding electrical contacts disposed on different mechanism modules can improve the reliability of the electrical connection. Similar to first electrical contacts 103, the type of one of the second electrical contact 113 also includes a rigid metal pin and an elastic conductive member. Preferably, in the embodiment of the present invention, the second electrical contact 113 is a conductive spring. Similarly, the conductive spring can improve the electrical connection performance. A groove is also arranged around the area where the second electrical contact 113 is disposed, and a sealing member 115 is arranged in the groove. Similarly, the elasticity of the conductive spring can further improve the electrical connection performance.

Preferably, in the embodiment of the present invention, the two ends of the conductive spring have different diameters. And the diameter of the end exposed to the outside of the infusion mechanism module 110 is shorter than that of the end inside the infusion mechanism module 110. In this way, the conductive spring can be held in the case because of the longer diameter, thus, when the control mechanism module 100 is not installed on the infusion mechanism module 110, the longer diameter of the inner end can prevent the conductive spring from detaching from the infusion mechanism module 110.

The embodiment of the present invention does not limit the position where second electrical contacts 113 are arranged, as long as it can be electrically connected to the corresponding first electrical contacts 103. Preferably, in the embodiment of the present invention, the upper case 111*a* of the infusion mechanism module 110 includes a convex portion 114 where the second electrical contacts 113 are disposed, as shown in FIG. 2*a*. The shape of the convex portion 114 corresponds to that of the concave 104 disposed on the control mechanism module 100, allowing the two portions to tightly fit each other and press the first electrical contacts 103 and the corresponding second electrical contacts 113 against each other to realize electrical connection.

In other embodiments of the present invention, the convex portion 114 may be provided on the lower case 111*b*, or when the infusion mechanism module 110 includes a integral case, the convex portion 114 is a part of the integral case, which is not specifically limited herein.

The method of assembling the control mechanism module 100 and the infusion mechanism module 110 to each other includes pressing the control mechanism module 100 on the infusion mechanism module 110 along with the thickness direction of the infusion mechanism module 110, thereby engaging the first engaging portion 102 and the second engaging portion 112. Or pressing the control mechanism module 100 on the infusion mechanism module 110 along with the length direction of the infusion mechanism module 110. Or alternatively, the control mechanism module 100 can be pressed along with any angle between the thickness direction and the length direction of the infusion mechanism module 110, making the first engaging portion 102 and the second engaging portion 112 engaged with each other. Preferably, in the implementation of the present invention, the method of which the control mechanism module 100 and the infusion mechanism module 110 are assembled with each other is to press the control mechanism module 100 on the infusion mechanism module 110 along with the thickness direction of the infusion mechanism module 110, making the first engaging portion 102 and the second engaging portion 112 engaged with each other, as shown the installation direction in FIG. 2*b*.

In the embodiment of the present invention, the lower case 111*b* of the infusion mechanism module 110 further includes an outward extending portion 116, and a block 117 is provided on the outside of the outward extending portion 116, as shown in FIG. 2*a*. As mentioned above, the control mechanism module 100 is pressed to the engaging position along the thickness direction of the infusion mechanism module 110, thus the block 117 can prevent the control mechanism module 100 from detaching along the length direction of the infusion mechanism module 110, ensuring the normal operation of the infusion device. Obviously, in another embodiment of the present invention, if the control mechanism module 100 is pressed to the engaging position along with other directions, the control mechanism module 100 can also be prevented from detaching from the infusion mechanism module 110 by adjusting the position of the block 117.

It should be noted here that "outward" and "outside" are relative to the main body of the infusion mechanism module 110, and belong to a concept of relative position, whose position relationship is shown in FIG. 2*a* or FIG. 2*b*. The "outside" below has the same meaning as here.

In the embodiment of the present invention, the outer end of the outward extending portion 116 is also provided with a pressing portion 118 for releasing the blocking effect of the block 117. While the user is replacing the infusion mechanism module 110, a finger presses the pressing portion 118, releasing the control mechanism module 100 from the block 117. Then, the user can remove the control mechanism module 100 from the infusion mechanism module 110 with another two fingers.

Another embodiment of the present invention can also be provided with an unlocking hole 119 disposed in the inner side of the block 117. While the pressing portion 118 is being pressed, a finger can enter the unlocking hole 119, thereby pushing the control mechanism module 100 out to separate the control mechanism module 100 from the infusion mechanism module 110. In the embodiment of the present invention, the unlocking hole 119 is square. The square unlocking hole 119 can facilitate smooth entry of fingers. In other embodiments of the present invention, the unlocking hole 119 may also have other shapes, which is not specifically limited here.

The lower case 111*b* of the infusion mechanism module 110 is also provided with one or more crease grooves 140. Two crease grooves 140 are provided on both sides of the unlocking hole 119, as shown in FIG. 2*c* and FIG. 2*d*. After the crease groove 140 is provided, the thickness or width of the lower case 111*b* at the position of the crease groove 140 is reduced. When the user presses the pressing portion 118, the lower case 1/1*b* is easy to be broken at the position of the crease groove 140, and the blocking of the control mechanism module 100 by the block 117 is more smoothly released.

Preferably, in the embodiment of the present invention, two crease grooves 140 are provided at the two ends of the block 117 respectively, as shown in FIG. 2*c*. In another embodiment of the present invention, the crease groove 140 is provided on two corresponding lateral sides of the unlocking hole 119, as shown in FIG. 2*d*.

The infusion mechanism module 110 of the embodiment of the present invention is further provided with an infusion needle unit 121 for infusing the drug under the skin.

A medical tape 120 is also provided on the bottom of the lower case 111*b* for attaching the infusion device on the surface of the user's skin.

FIG. 3*a* and FIG. 3*b* are respectively two schematic views of the internal mechanism module 130 of the infusion mechanism module 110 of the embodiment of the present invention from two perspectives.

In the embodiment of the present invention, the internal mechanism module 130 includes mechanical units and electronic control units, used to realize the infusion function, such as a drug reservoir 131, a drug outlet 132, a power supply 133, a driving wheel 134, a screw 135, a circuit board (not shown), a driving unit (not shown), etc. The movement of the driving unit drives the driving wheel 134 to rotate, thus making the screw 135 push the piston (not shown) in the drug reservoir 131 to forward, realizing the drug infusion.

In the embodiment of the present invention, the power supply 133 is a conventional button battery. In other embodiments of the present invention, the power supply 133 may also be other types of batteries, as long as it can meet the requirements for supplying power to the infusion device. Preferably, in the embodiment of this present invention, the type of the power supply 133 is double-row battery pack, that is, two rows of button batteries are respectively arranged on both sides of the driving wheel 134, as shown in FIG. 3*b*. Conventionally, the discharge capacity of button batteries is low. The double-row button battery pack can reduce the discharge level of each battery, thereby extending the service life of the battery. Furthermore, the double-row design of the power supply 133 can make full use of the internal space and improve the integration of the internal mechanism module in the infusion device.

The infusion mechanism module 110 in the embodiment of the present invention is also provided with a circuit board or multiple three-dimensional circuits coated on the surface of a part of the mechanism module for supplying power to specific structural units. The circuit board is a hard/rigid circuit board or a flexible circuit board. Preferably, in the embodiment of the present invention, the circuit board is a flexible circuit board. The shape of the flexible circuit board is plastic, allowing it to be flexibly designed according to the internal space of the infusion mechanism module 110. At the same time, multiple connection ends can be provided on the flexible circuit board to be electrically connected to second electrical contacts 113, thereby connecting the circuits of the control mechanism module 100 and the infusion mechanism module 110, letting the infusion device to perform drug infusion function.

An elastic conductor 136 is also provided inside the infusion mechanism module 130, as shown in FIG. 3*a*. The elastic conductor 136 is electrically connected to the power supply 133 and the specific connection end on the circuit board (or three-dimensional circuit), thereby supplying power to specific structural units.

Similar to the elastic conductive member above mentioned, the type of the elastic conductor 136 includes a conductive spring, a conductive leaf spring, a conductive rubber, a conductive silica gel, etc., which are not specifically limited herein, as long as they can meet the requirements for electrically connecting the power supply 133 to specific connection ends on the circuit board (or three-dimensional circuit). Preferably, in the embodiment of the present invention, the elastic conductor 136 is the conductive leaf spring. Obviously, since the infusion mechanism module 110 has a double-row battery pack, the multiple conductive leaf springs are also designed as a double-row pack, as shown in FIG. 3*a*.

The elastic conductor 136 can realize direct electrical connection between the power supply 133 and the specific structural units, which helps to optimize the internal circuit design and reduce the complexity of the internal mechanism module.

In summary, the present invention discloses a skin patch drug infusion device. The alarm is non-closed arranged in the control mechanism module, reducing the energy consumption of the alarm, optimizing the power consumption configuration of the infusion device and saving production costs.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A skin patch drug infusion device, comprising:

a control mechanism module provided with multiple first engaging portions and a first electrical connection exposed on a surface of the control mechanism module; and an infusion mechanism module including a case, with a second electrical connection exposed on a surface of the case and second engaging portions engaged with the first engaging portions, wherein when the control mechanism module and the infusion mechanism module are assembled with each other, the first engaging portions and the second engaging portions are engaged, the first electrical connection and the second electrical connection are electrically connected to each other, thereby the control mechanism module and the infusion mechanism module are electrically connected to each other; and an alarm, not enclosed within the control mechanism module, wherein the case includes an upper case and a lower case, wherein the lower case further includes an outward extending portion, and a block is provided on an outside of the outward extending portion.

2. The skin patch drug infusion device of claim 1, wherein the alarm is one or a combination of a lighting alarm, audio alarm and vibration alarm, or an alarm with multiple alarm signals of light, sound, or vibration.

3. The skin patch drug infusion device of claim 2, wherein the alarm is a buzzer.

4. The skin patch drug infusion device of claim 3, wherein at least a non-closed area is provided on a housing of the control mechanism module.

5. The skin patch drug infusion device of claim 4, wherein the non-closed area is a sound-permeable outlet.

6. The skin patch drug infusion device of claim 5, wherein the housing of the control mechanism module includes an upper housing and a lower housing, the sound-permeable outlet is arranged on the lower housing.

7. The skin patch drug infusion device of claim 6, wherein a waterproof sound-permeable membrane is disposed between the sound-permeable outlet and the buzzer.

8. The skin patch drug infusion device of claim 7, wherein the first engaging portions include some-of at least one hook, at least one connecting block, at least one hole and at least one slot, and the second engaging portions include some of at least one hook, at least one connecting block, at least one hole and at least one slot, the first engaging portions and the second engaging portions are engaged with each other.

9. The skin patch drug infusion device of claim 8, wherein the first engaging portions and the second engaging portions are first electrical contacts and second electrical contacts.

10. The skin patch drug infusion device of claim 9, wherein one of the first electrical contacts is a rigid metal pin or an elastic conductive member, or one of the second electrical contacts is a rigid metal pin or an elastic conductive member.

11. The skin patch drug infusion device of claim 10, wherein the elastic conductive member includes a conductive spring, a conductive leaf spring, a conductive rubber, or a conductive silica gel.

12. The skin patch drug infusion device of claim 11, wherein one of the first electrical contacts is a rigid metal pin while one of the second electrical contacts is a conductive spring, and a groove, within which a sealing element is provided, is disposed around an area where the second electrical contacts are disposed.

13. The skin patch drug infusion device of claim 12, wherein a plurality of connection ends are provided in the infusion mechanism module, and a plurality of compressed conductive springs are respectively electrically connected to the connection ends.

14. The skin patch drug infusion device of claim 13, wherein a flexible circuit board on which the connection ends are disposed is further provided in the infusion mechanism module.

15. The skin patch drug infusion device of claim 1, wherein a pressing portion is provided on the outside of the outward extending portion.

* * * * *